US009950049B2

(12) United States Patent
Godfrin et al.

(10) Patent No.: US 9,950,049 B2
(45) Date of Patent: Apr. 24, 2018

(54) COMPOSITION AND THERAPEUTIC ANTI-TUMOUR VACCINE

(71) Applicant: ERYTECH PHARMA, Lyons (FR)

(72) Inventors: Yann Godfrin, Lyons (FR); Alice Banz, Lyons (FR)

(73) Assignee: ERYTECH PHARMA, Lyons (FR)

( * ) Notice: Subject to any disclaimer, the term of this patent is extended or adjusted under 35 U.S.C. 154(b) by 0 days.

(21) Appl. No.: 15/154,273

(22) Filed: May 13, 2016

(65) Prior Publication Data

US 2016/0324946 A1 Nov. 10, 2016

Related U.S. Application Data

(62) Division of application No. 12/672,094, filed as application No. PCT/EP2008/060492 on Aug. 8, 2008, now Pat. No. 9,364,504.

(60) Provisional application No. 60/954,917, filed on Aug. 9, 2007.

(30) Foreign Application Priority Data

Aug. 8, 2007 (FR) ..................................... 07 05767

(51) Int. Cl.

| | |
|---|---|
| ***A61K 35/28*** | (2015.01) |
| ***A61K 35/26*** | (2015.01) |
| ***C12N 5/00*** | (2006.01) |
| ***A61K 38/00*** | (2006.01) |
| ***A61K 39/00*** | (2006.01) |
| ***A61K 35/18*** | (2015.01) |
| ***A61K 47/02*** | (2006.01) |
| ***A61K 47/22*** | (2006.01) |
| ***A61K 47/26*** | (2006.01) |
| ***C07K 16/28*** | (2006.01) |

(52) U.S. Cl.

CPC .......... *A61K 39/0011* (2013.01); *A61K 35/18* (2013.01); *A61K 47/02* (2013.01); *A61K 47/22* (2013.01); *A61K 47/26* (2013.01); *C07K 16/2806* (2013.01); *A61K 2039/5154* (2013.01); *A61K 2039/5156* (2013.01); *A61K 2039/55522* (2013.01); *A61K 2039/55561* (2013.01); *A61K 2039/572* (2013.01); *A61K 2039/6056* (2013.01)

(58) Field of Classification Search

None

See application file for complete search history.

(56) References Cited

U.S. PATENT DOCUMENTS

| | | | |
|---|---|---|---|
| 4,321,259 | A | 3/1982 | Nicolau et al. |
| 4,327,710 | A | 5/1982 | Deloach et al. |
| 4,478,824 | A | 1/1984 | Franco et al. |
| 4,752,586 | A | 6/1988 | Ropars et al. |
| 4,965,857 | A | 10/1990 | Auracher et al. |
| 5,372,942 | A | 12/1994 | McGarrity |
| 5,589,389 | A | 12/1996 | Pages et al. |
| 5,612,207 | A | 3/1997 | Nicolau et al. |
| 5,916,793 | A | 6/1999 | Filpula |
| 6,139,836 | A | 10/2000 | Magnani et al. |
| 6,218,166 | B1 | 4/2001 | Ravindranath et al. |
| 6,610,702 | B2 | 8/2003 | Lehn et al. |
| 6,737,259 | B1 | 5/2004 | Clark |
| 7,037,500 | B1 | 5/2006 | Silverstein et al. |
| 2006/0002915 | A1 | 1/2006 | Min et al. |
| 2006/0188490 | A1 | 8/2006 | Hoerr et al. |
| 2008/0261262 | A1 | 10/2008 | Godfrin et al. |
| 2008/0274092 | A1 | 11/2008 | Godfrin et al. |

FOREIGN PATENT DOCUMENTS

| | | |
|---|---|---|
| EP | 0 414 007 | 2/1991 |
| GB | 1051382 | 12/1966 |
| JP | 2035081 | 2/1990 |
| JP | 2053490 | 2/1990 |
| JP | 6062867 | 3/1994 |
| WO | WO 98/39027 | 9/1998 |

OTHER PUBLICATIONS

Cabantchik et al BBA, 1975, v.382, pp. 621-633).*

International Search Report for PCT/EP2008/060492.

Murray et al: "The mouse immune response to carrier erythrocyte entrapped antigens" Vaccine, Butterworth Scientific. Guildford, GB, vol. 24, No. 35-36, (Aug. 28, 2006), pp. 6129-6139.

Hamidi et al: "Applications of carrier erythrocytes in delivery of biopharmaceuticals" Journal of Controlled Release, Elsevier, Amsterdam, NL, vol. 118, No. 2, (Mar. 2007), pp. 145-160.

Millan C G et al: "Drug, enzyme and peptide delivery using erythrocytes as carriers" Journal of Controlled Release, Elsevier, Amsterdam, NL, vol. 95, No. 1, (Feb. 20, 2004), pp. 27-49.

Hamidi Mehrdad et al: "Preparation and validation of carrier human erythrocytes loaded by bovine serum albumin as a model antigen/protein" Drug Delivery, Academic Press, Orlando, FL, US, vol. 14, No. 5, (Jul. 2007), pp. 295-300.

Corinti Silvia et al: "Erythrocytes deliver Tat to interferon-gamma-treated human dendritic cells for efficient initiation of specific type 1 immune responses in vitro." Journal of Leukocyte Biology Apr. 2002,. vol. 71, No. 4, (Apr. 2002), pp. 652-658.

(Continued)

*Primary Examiner* — Michail Belyavskyi

(74) *Attorney, Agent, or Firm* — B. Aaron Schulman, Esq.; Stites & Harbison, PLLC

(57) ABSTRACT

The invention relates to a composition which induces, in a host, a cytotoxic cell response directed against cells expressing an antigen, in particular tumor cells, and which comprises red blood cells containing said antigen. These red blood cells may be in the form of an immune complex with an immunoglobulin, in particular IgG, which recognizes an epitope at the surface of the red blood cells, and/or be heat-treated or chemically treated so as to promote phagocytosis of said red blood cells by dendritic cells. As a variant, the red blood cells may be xenogenic red blood cells. The invention also relates to a therapeutic especially anti-tumor vaccine containing such a composition.

22 Claims, 2 Drawing Sheets

(56) References Cited

OTHER PUBLICATIONS

Figure 1:
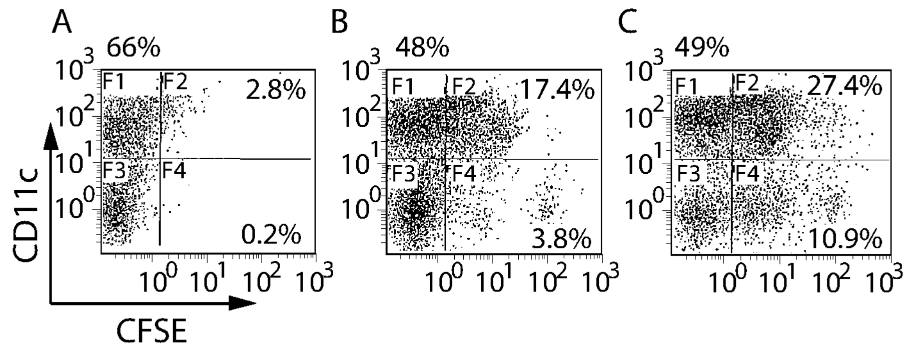

Bouvier M et al: "A novel approach for a specific delivery of glucocerebrosidase in bone marrow Gaucher cells" Molecular Genetics and Metabolism. vol. 93, No. 2, (Feb. 2008), p. S17.
Eymard et al, "Cell Therapy and Prostate Cancer", 2003, pp. 734-743, vol. 90, No. 8-9, Dossier Thematique.
Banchereau et al, "Dendritic Cells as Vectors for Therapy", Aug. 10, 2001, pp. 271-274, vol. 106, Cell.
Bigbee et al, "Monoclonal Antibodies Specific for the M- and N-Forms of Human Glycophorin A*" 1983, pp. 1353-1362, vol. 20, No. 12, Molecular Immunology.
Segura et al, "Interaction of Mouse Dendritic Cells and Malaria-Infected Erythrocytes: Uptake, Maturation, and Antigen Presentation", 2006, pp. 441-450, vol. 176, Journal of Immunology.
Hervas-Stubbs et al, "TLR3 ligand stimulates fully functional memory CD8+T cells in the absence of CD4+ T-cell help", Jun. 15, 2007, pp. 5318-5326, vol. 109, No. 12, Immunobiology.
Lou et al, "Plasmacytoid Dendritic Cells Synergize with Myeloid Dendritic Cells in the Induction of Antigen-Specific Antitumor Immune Responses", 2007, pp. 1534-1541, vol. 178, The Journal of Immunology.
Boberg et al, "Immunization with HIV Protease Peptides Linked to Syngeneic Erythrocytes", 2007, pp. 1-4, vol. 2, No. 9, Infectious Agents and Cancer.
Dominici et al, "Red Blood Cell-Mediated Delivery of Recombinant HIV-1 Tat Protein in Mice Induces Anti-Tat Neutralizing Antibodies and CTL", 2003, pp. 2073-2081, Vaccine.
Regnault et al, "Fcγ Receptor-mediated Induction of Dendritic Cell Maturation and Major Histocompatibility Complex Class I-restricted Antigen Presentation after Immune Complex Internalization", Jan. 18, 1999, pp. 371-380, vol. 189, No. 2, J. Exp. Med.
Yang et al, "Carrier erythrocytes and its application in targeting chemotherapy", pp. 1015-1018, vol. 17, No. 11, Journal of Medical Postgraduates.
Boucher Laurence et al: "Internalization and distribution of inositol hexakisphosphate in red blood cells", Biotechnology and Applied Biochemistry, vol. 24, No. 1, 1996, pp. 73-78.
Millan C G et al: "Drug enzyme and peptide delivery using erythrocytes as carriers", Journal of Controlled Release, Elsevier Science Publishers B.V. Amsterdam, NL, vol. 95, No. 1, Feb. 20, 2004 (Feb. 20, 2004), pp. 27-49.
Didelon J et al: "Validation of a test of the red cell membrance osmotic resistance", Clinical Hemorheology and Microcirculation, vol. 23, No. 1, 2000, pp. 31-42.
Kravtzoff R et al: "Erythrocytes as carriers for L-asparaginase Methodological and mouse in-vivo studies", The Journal of Pharmacy and Pharmacology Jul. 1990, vol. 42, No. 7, Jul. 1990 (Jul. 1990), pp. 473-476.
Philip Seeman. "Transient holes in the erythrocyte membrance during hypotonic hemolysis and stable holes in the membrane after lysis by saponin and lysolecithin", J. Cell. Biol. 1967, 32(1): 55-70.
Labrude et al, "L'Hematie Vecteur D'Enzyme et de Medicament", 1985, pp. 181-187, vol. 36, No. 4, Lyon Pharmaceutique.
Sadahiro et al, "Pharmacokenetic of 5-Fluorouracil Following Hepatic Intra-arterial Infusion in a VX2 Hepatic Metastasis Model", 2003, pp. 377-381, vol. 33, No. 8, Jpn J Clin Oncol.
Hamidi et al, "Carrier Erythrocytes: An Overview", 2003, pp. 9-20, vol. 10, No. 9, Drug Delivery.
Bax et al, "Survival of human carrier erythrocytes in vivo", 1999, pp. 171-178, vol. 96, Clinical Science.
Hussain et al, "Erythrocyte Osmotic Fragility in Man: Variation with Age and Sex", 1984, pp. 716-718, vol. 54, No. 4, Br. J. Haematol.
Kolanjiappan et al, "Measurement of erythrocyte lipids, lipid peroxidation, antioxidants and osmotic fragility in cervical cancer patients", 2002, pp. 143-149, Clinica Chimic Acta 326.
Wang et al, "Evaluation of immunologic crossreaction of antiasparaginase antibodies in acute lymphoblastic leukemia (ALL) and lymphoma patients", 2003, pp. 1583-1588, vol. 17, Leukemia.
Schrijvers, Dirk, "Role of Red Blood Cells in Pharmacokinetics of Chemoterapeutic Agents", 2003, pp. 779-791, vol. 42, No. 9, Clin. Pharmacokinet.
Didelon et al, "Osmotic fragility of the erythrocyte membrane: characterization by modeling of the transmittance curve as a function of the NaCl concentration", 2000, pp. 409-416, Biorheology 37.
Zocchi et al, "Encapsulation of doxorubicin in liver-targeted erythrocytes increases the therapeutic index of the drug in a murine metastatic model", Mar. 1989, pp. 2040-2044, vol. 86, Proc. Natl. Acad. Sci., USA.
Bailleul et al, "Internalization of Various Allosteric Effectors of Hemoglobin in Human Erythrocytes", 1991, pp. 9-16, vol. 81, Advances in the Biosciences.
Deleuze et al, "Enhanced $O_2$ transportation during cardiopulmonary bypass in piglets by the use of inositol hexaphoshate loaded red blood cells", 1992, pp. 239-242, vol. 15, No. 4, The International Journal of Artificial Organs.
Ropars et al, "Engineered erythrocytes: influence of $P_{50}$ rightward shift and oxemia on oxygen transport to tissues", Jul. 1998, pp. 508-512, Medical & Biological Engineering & Computing.
Holtsberg et al, "Poly(ethylene glycol) (PEG) conjugated arginine deiminase: effects of PEG formulations on its pharmacological properties", Apr. 23, 2002, pp. 259-271, vol. 80, No. 1-3, Journal of Controlled Release, Elsevier, Amsterdam, Netherlands.
Park, et al, "Arginine deiminase: A potential inhibitor of angiogenesis and tumour growth", Sep. 1, 2003, pp. 907-914, vol. 89, No. 5, British Journal of Cancer.
Izzo et al., "Pegylated Arginine Deiminase Treatment of Patients With Unresectable Hepatocellular Carcinoma: Results From Phase I/II Studies", pp. 1815-1822, vol. 22, No. 10, May 15, 2004, Journal of Clinical Oncology.
Ensor et al., "Pegylated Arginine Deiminase (ADI-SS $PEG_{20,000mw}$) Inhibits Human Melanomas and Hepatocellular Carcinoma in Vitro and in Vivo", pp. 5443-5450, Cancer Research 62, Oct. 1, 2002.
Bomalaski et al., "Comparative Toxicity of Arginine Deiminase Formulated with Poly(Ethylene Glycol) 5000 or 20,000 and the Effects of Arginine", pp. 284-293, vol. 1, No. 5, 2003.
Ash, "Structure and Function of Arginases", pp. 2760S-2764S, Arginine Metabolism: Enzymology, Nutration, and Clinical Significance, American Society for Nutritional Sciences, 2004.
Albina et al ., "Arginine Metabolism in wounds", pp. E459-E467, The American Physiological Society, 1988.
Lind, "Arginine and Cancer[1]", pp. 2837S-2841S, Arginine Metabolism: Enzymology, Nutration, and Clinical Significance, American Society for Nutritional Sciences, 2004.
Mori et al., "Arginine Metabolic Enzymes, Nitric Oxide and Infection", pp. 2820S-2825S, Arginine Metabolism: Enzymology, Nutration, and Clinical Significance, American Society for Nutritional Sciences, 2004.
Lange et al., "Novel Roles for Arginase in Cell Survival, Regeneration, and Translation in the Central Nervous System", pp. 2812S-2817S, Arginine Metabolism: Enzymology, Nutration, and Clinical Significance, American Society for Nutritional Sciences, 2004.
Stuehr, "Enzymes of the L-Arginine to Nitric Oxide Pathway", pp. 2748S-2751S, Arginine Metabolism: Enzymology, Nutration, and Clinical Significance, American Society for Nutritional Sciences, 2004.
Curley et al., "Regression of hepatocellular cancer in a patient treated with arginine deiminase", Hepatogastroenterology. Sep.-Oct. 2003; 50 (53):1214-6.
Adriaenssens et al., "Hyperargininemia: The Rat as a Model for the Human Disease and the Comparative Response to Enzyme Replacement Therapy With Free Arginase and Arginase-Loaded Erythrocytes In Vivo", pp. 779-786, vol. 16, No. 5, Great Britain.
Thomas et al., "Enzymic degradation of plasma arginine using arginine deiminase inhibits nitric oxide production and protects mice from the lethal effects of tumour necrosis factor and endotoxin", pp. 581-587, Biochemical Society, (2002) 363, Great Britain.
Wei-Chiang, "Arginine Deiminase as an Innovative Anti-Breast Cancer Agent", pp. 1-2, Research Priorities, Innovative Treatment Modalities >New Drug Design: creative science, 2000, University of Southern California.

(56) References Cited

OTHER PUBLICATIONS

Gong et al., "Arginine deiminase and other antiangiogenic agents inhibit unfavorable neuroblastoma growth: potentiation by irradiation", pp. 723-728, Int. J Cancer. Sep. 20, 2003; vol. 106 No. 5.
Gong et al., "Arginine deiminase inhibits proliferation of human leukemia cells more potently than asparaginase by inducing cell cycle arrest and apoptosis", pp. 826-829, Leukemia, May 14, 2000.
Vellard, "The enzyme as drug: application of enzymes as pharmaceuticals", pp. 1-7 Current Opinion in Biotechnology, 2003.
Dillon et al., "Biochemical characterization of the arginine degrading enzymes arginase and arginine deiminase and their effect on nitric oxide production", Med. Sci. Monit, pp. 248-253, Basic Research, 2002.
Van Broeckhoven et al, "Measurement of Arginine Transport in Human Erythrocytes Using Their Intrinsic Arginase Activity: Implications for the Treatment of Familial Hyperargininemia", 1982, pp. 209-216, vol. 126, Clinica Chimica Acta.
Spector et al, "Comparison or Arginase Activity in Red Blood Cells of Lower Mammals, Primates, and Man: Evolution to High Activity in Primates", 1985, pp. 1138-1145, Am. J. Hum. Genet.

* cited by examiner

COMPOSITION AND THERAPEUTIC ANTI-TUMOUR VACCINE

CROSS-REFERENCE TO RELATED APPLICATIONS

This application is a divisional application of U.S. Ser. No. 12/672,094, having a filing date of Feb. 4, 2010, which was a 371 application of International application PCT/EP08/60492, filed Aug. 8, 2008, which claimed the benefit of U.S. provisional patent application 60/954,917, filed Aug. 9, 2007, and French patent application, FR 07 05767, filed Aug. 8, 2007, all of said applications incorporated herein by reference.

FIELD OF THE INVENTION

The present invention relates to a composition which induces, in a host, a cytotoxic response for anti-tumour purposes, and also to a therapeutic anti-tumour vaccine containing this composition.

BACKGROUND OF THE INVENTION

The natural immune response against tumour antigens is relatively ineffective and various mechanisms allowing tumours to escape the anti-tumour immune response have been identified. Conventional vaccine approaches generate humoral responses which prove to be insufficient.

Strategies aimed at developing a cytotoxic response based on antigen-presenting cells (APCs), in particular based on dendritic cells, have been studied. The principle consists in specifically destroying the cancer cells of a patient by stimulating said patient's own immune defences.

Dendritic cells are antigen-presenting cells (APCs) that are very effective in generating cytotoxic effectors specific for tumour cells. They are capable of phagocytizing apoptotic cells or apoptotic bodies originating from tumour cells, and then of presenting the tumour antigens, in association with MHC class I and II molecules, to T lymphocytes. Thus, the dendritic cell is capable of initiating the proliferation and the generation of a clone of specific cytolytic T lymphocytes. At the end of this reaction, the killer lymphocytes thus differentiated leave the lymphoid compartment so as to circulate in the organism and bind in the tumour. Recognition of the antigens expressed by a tumour then induces a lytic signal and brings about the destruction of the tumour cells.

Several anti-cancer vaccine strategies targeting dendritic cells have been studied (Eymard J C, Bernard J, Bull Cancer. 2003, 90(8-9):734-43). Some are based on manipulating the dendritic cells in vitro, and others are based on stimulating the dendritic cells in vivo. In the first case, the dendritic cells are differentiated from blood cells taken from the patient: they are cultured and matured, "pulsed", i.e. stimulated, ex vivo with tumour peptides, tumour lysates, apoptotic tumour cells, or heat shock proteins extracted from autologous tumours, and finally reinjected into the patient. In the second case, the stimulation of the dendritic cells is carried out after injection, into the patient, of peptides, proteins, irradiated tumour cells or else viruses containing the antigenic peptide targeting the dendritic cells. However, the cytotoxic response obtained is rarely accompanied by clinical efficacy. The activation of the dendritic cell "conditions" its ability to effectively activate the cytolytic T lymphocyte. The level of activation of dendritic cells appears to be a delicate point in this vaccine strategy.

The use of dendritic cells ex vivo for obtaining an anti-tumour vaccine raises a certain number of issues on: the state of maturation of the dendritic cells, the number of cells to be injected, the route, the site and the frequency of injection for producing dendritic cells capable of migrating to the secondary lymphoid organs and of inducing an effective cytotoxic T response (Banchereau J, Schuler-Thurner B, Palucka A K, Schuler G. [Dendritic cells as vectors for therapy] Cell. 2001, 10, 106(3): 271-4.).

The activation of dendritic cells in vivo is, for its part, limited by the weak immunogenic capacity of tumour antigens and the difficulty in activating dendritic cells at a sufficient level.

The use of red blood cells as carriers for transporting antigens, encapsulated in the red blood cells or bound to their surface, and delivered to the APCs has been envisaged in several publications. The triggered immune responses have been investigated in vitro and in vivo.

Hamidi et al. have recently described the encapsulation of BSA (bovine serum albumin) as a model of an antigen in human red blood cells (Hamidi M et al., Drug Deliv., 2007; 14(5):295-300 and Int J Pharm., 2007, 29, 338(1-2): 70-8). The authors suggested the use of red blood cells as a vector for the presentation of antigens to APCs of the reticuloendothelial system (RES). In another review published by Hamidi et al. (J. Control. Release, 2007, 118(2): 145-60), the authors indicated that a certain number of strategies have been studied to promote targeting of the RES, said targeting being promoted by ageing of the red blood cells, leading to their uptake for lysis. Other routes were mentioned, such as exposure of red blood cells to stabilizing agents, in particular crosslinking agents, coating of red blood cells with anti-RH antibodies, of IgG type to target the spleen or of IgM type to target the liver, heat shock, or exposure to oxidizing agents, enzymes or antibiotics.

A humoral immune response can be obtained in vivo after immunization with antigen-loaded red blood cells. The study carried out by Murray et al. made it possible to detect, in mice, IgG immunoglobulins after intravenous injection of murine red blood cells loaded with one of the following four antigens: KLH (Keyhole Limpet Haemocyanin), BSA (Bovine Serum Albumin), CTB (Cholera Toxin b Subunit) and ADA (Bovine Adenosine Deaminase). Detection of IgG1 and IgG3, which are predominant immunoglobulin isotypes during a Th2 response, and of IgG2, immunoglobulin isotype which is a marker for a Th1 response, would suggest the involvement of both types of immune responses, the humoral response and the cellular response (Murray A M et al., Vaccine., 2006 28, 24(35-36): 6129-39).

Another formulation of antigens used with red blood cells has been tested by Dominici et al. The Tat protein of the HIV-1 virus was anchored to the surface of mouse red blood cells by means of avidin/biotin coupling. The immunization of mice by intraperitoneal injection with this antigen formulation, internalized by dendritic cells, triggered a humorally-mediated immune response in vivo. Isotype characterization of the immunoglobulins detected indicates the induction of Th1 and Th2 responses. The anti-Tat cytotoxic activity was shown in vitro, by the conventional chromium-release technique, for the mice treated with red blood cells coupled to the antigens (Dominici S et al., Vaccine., 2003 16, 21(17-18): 2073-81).

A cellular response has been demonstrated in vitro by Corinti et al. with the same formulation. Phagocytosis of the red blood cells conjugated with Tat protein, by dendritic cells derived from human monocytes, was shown, as was the induction of CD4+ and CD8+ responses. Moreover, maturation of dendritic cells in the presence of interferon gamma promoted the type I immune response (Corinti S. et al., Leukoc. Biol. 2002, 71(4): 652-8).

Boberg et al. injected mice intraperitoneally with a vaccine constituted of peptides derived from the HIV-1 protease anchored at the surface of mouse red blood cells by means of the avidin/biotin system. They chemically modified red blood cells with the aim of promoting their recognition by APCs, but a weak immune reaction was obtained. They concluded that the small amount of antigens delivered, due to the limited loading of red blood cells with antigenic peptides and blood volume injected was not compensated for by the chemical modification of the carriers supposed to promote antigen recognition by APCs (Boberg A. et al., Infect. Agents Cancer., 2007, 182: 9).

SUMMARY OF THE INVENTION

The present invention aims to provide compositions and vaccines that can be used in the treatment of cancers, according to an immunotherapy approach.

An object of the invention is therefore a composition which induces, in a host, a cytotoxic cellular response directed against tumour cells, and which comprises red blood cells containing a tumour antigen.

The term "host" refers preferably to humans, but also to animals, in particular pets (especially dogs or cats) and animals for sport (especially horses).

According to the invention, the red blood cells contain, i.e. encapsulate, the antigen, which means that the antigen is or is essentially inside the red blood cell.

Said red blood cells are preferably designed, selected or modified so as to promote phagocytosis thereof by APCs, and most particularly by dendritic cells. In particular, said red blood cells are designed, selected or modified so as to promote phagocytosis thereof in the spleen and the liver, the essential objective being to target APCs of the spleen.

In a preferred embodiment, the compositions according to the invention comprise red blood cells which contain the antigen and target the spleen. The composition promotes phagocytosis of these red blood cells by the APCs, in particular the dendritic cells, in the spleen.

BRIEF DESCRIPTION OF THE DRAWING FIGURES

FIG. 1: Measurement of the phagocytosis of "antigen-loaded" red blood cells treated with the anti-TER 119 antibody, by spleen dendritic cells in vitro.

Figure 2:
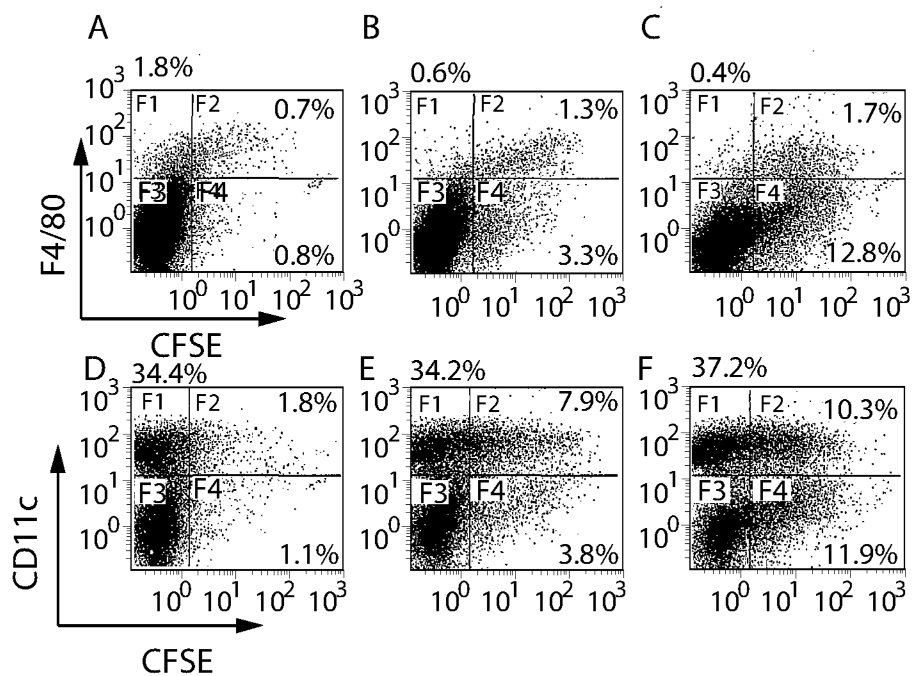

FIG. 2: Measurement of the phagocytosis of "antigen-loaded" red blood cells treated with the anti-TER 119 antibody or heat-treated, by spleen macrophages and dendritic cells in vivo.

Figure 3:
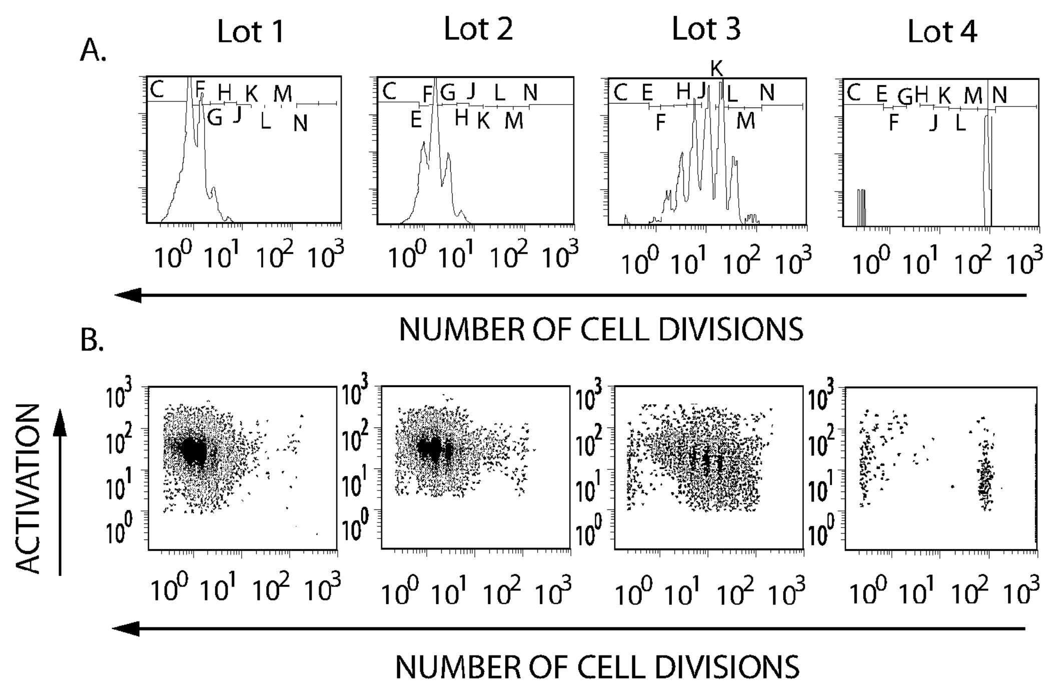

FIG. 3: Graph illustrating the proliferation and activation of ovalbumin-specific CD4 T cells 3 days after injection into mice.

(A) Cell division induces a reduction in the intensity of CFSE fluorescence. OVA-specific CD4 T cells lose half of their fluorescent material on each division. The peak observed for batch 4 represents undivided cells having a large CFSE content. All of the other peaks represent cells which have undergone 1, 2, 3, 4, 5, 6 or 7 cell divisions. When the cells have divided more than 8 times, the CFSE content of the cells is practically zero.

(B) CD44 cell activation marker expression is represented as a function of the number of divisions occurring.

DETAILED DESCRIPTION OF EXEMPLARY EMBODIMENTS

According to a first embodiment, the red blood cells contain a tumour antigen and are in the form of an immune complex with an immunoglobulin which recognizes an epitope at the surface of said red blood cells, so as to promote the phagocytosis of said red blood cells, in particular by dendritic cells. The composition also makes it possible to promote phagocytosis by macrophages. Preferably, the immunoglobulin is an immunoglobulin G.

The formation of the immune complex involves red blood cells and at least one antibody, preferably of IgG subtype. Dendritic cells have, at their surface, receptors for the constant Fc region of immunoglobulins G (IgGs). These receptors are capable of triggering phagocytosis or internalization of the antigen-IgG immune complexes thus formed and of promoting antigen presentation by MHC class I and II molecules, resulting in the generation of $CD4^+$ helper lymphocytes and especially $CD8^+$ cytotoxic lymphocytes (A. Regnault et al., J. Exp. Med., Janvier 1999, 189(2): 371-80).

As antibodies which are suitable, mention may be made of anti-rhesus antibodies, anti-glycophorin A antibodies and anti-CR1 antibodies (CR1=complement receptor type 1). Anti-glycophorin A antibodies (A. Bigbee et al., Mol. Immunol., December 1983, 20(12): 1353-62) are a preferred modality.

Preferably, the red blood cells of human origin that are used to form an immune complex are heterologous red blood cells originating from a donor.

According to a second embodiment, the red blood cells contain a tumour antigen and are heat or chemically modified, so as to promote phagocytosis of said red blood cells, in particular by dendritic cells. The composition also makes it possible to promote phagocytosis by macrophages.

The heat treatment is in particular carried out under the following conditions: heating of red blood cells for about 15 minutes to about 90 minutes, preferably from about 25 to about 50 minutes, at a temperature of between about 42 and about 55° C., preferably between about 47 and about 51° C. Typically, red blood cells are heated for about 30 minutes at between about 48 and about 50° C., for example at about 48° C.

The chemical treatment is carried out using agents which modify the surface of red blood cells, and in particular bridging or crosslinking agents such as bis(sulphosuccinimidyl) suberate (BS3 or $BS^3$), glutaraldehyde or neuraminidase.

In a particular embodiment, at least two methods of targeting are combined, and, for example, the composition then comprises antigen-containing red blood cells which are in the form of an immune complex and are heat or chemically treated so as to promote their uptake in the spleen and/or the liver, preferably the spleen, and phagocytosis by APCs, in particular by dendritic cells.

In a third embodiment, the antigen-containing red blood cells are xenogenic. Injection of xenogenic red blood cells into humans results in the binding of the patient's natural antibodies to the injected red blood cells. The immune complex thus formed promotes phagocytosis by APCs, in particular by dendritic cells. Preferably, said red blood cells are of porcine origin.

In a particular embodiment, the xenogenic red blood cells are heat or chemically modified so as to promote phagocytosis thereof.

The composition according to the invention may comprise one or more tumour antigens. When there are several tumour antigens, said tumour antigens are preferably selected so as to induce an immune response against one type of tumour or of tumour cells.

The composition preferably comprises at least two tumour antigens representative of the tumour to be treated. The objective is to generate several clones of cytotoxic T lymphocytes which each recognizes a specific antigenic peptide so as to develop a more effective immune response.

In a particular embodiment, the composition comprises at least two populations of red blood cells, each encapsulating a different antigen.

The most well known antigens that can be used herein are indicated in the tables below, where they are classified by category.

Unique Antigens:

| Gene/protein | Tumour |
|---|---|
| alpha-actinin-4 | Lung carcinoma |
| ARTC1 | Melanoma |
| BCR-ABL fusion protein (b3a2) | Chronic myeloid leukaemia |
| B-RAF | Melanoma |
| CASP-5 | Colorectal, gastric and endometrial carcinoma |
| CASP-8 | Head and neck squamous cell carcinoma |
| beta-catenin | Melanoma |
| Cdc27 | Melanoma |
| CDK4 | Melanoma |
| CDKN2A | Melanoma |
| COA-1 | Colorectal carcinoma |
| dek-can fusion protein | Myeloid leukaemia |
| EFTUD2 | Melanoma |
| Elongation factor 2 | Squamous cell carcinoma of the lung |
| ETV6-AML1 fusion protein | Acute lymphoblastic leukaemia |
| FN1 | Melanoma |
| GPNMB | Melanoma |
| LDLR-fucosyltransferaseAS fusion protein | Melanoma |
| HLA-A2d | Renal cell carcinoma |
| HLA-A11d | Melanoma |
| hsp70-2 | Renal cell carcinoma |
| KIAAO205 | Bladder tumour |
| MART2 | Melanoma |
| ME1 | "Non small cell" lung carcinoma |
| MUM-1f | Melanoma |
| MUM-2 | Melanoma |
| MUM-3 | Melanoma |
| neo-PAP | Melanoma |
| Myosin class I | Melanoma |
| NFYC | Squamous cell carcinoma of the lung |
| OGT | Colorectal carcinoma |
| OS-9 | Melanoma |
| pml-RARalpha-fusion protein | Promyelocytic leukaemia |
| PRDX5 | Melanoma |
| PTPRK | Melanoma |
| K-ras | Pancreatic adenocarcinoma |
| N-ras | Melanoma |
| RBAF600 | Melanoma |
| SIRT2 | Melanoma |
| SNRPD1 | Melanoma |
| SYT-SSX1 or -SSX2 fusion protein | Sarcoma |
| Triosephosphate Isomerase | Melanoma |
| FLT3-ITD | Acute myeloid leukaemia |
| p53 | Head and neck squamous carcinoma |

Antigens common to several tumours:

a) Tumour-Specific Antigens

| Genes |
|---|
| BAGE-1 |
| GAGE-1,2,8 |
| GAGE-3,4,5,6,7 |
| GnTVf |
| HERV-K-MEL |
| KK-LC-1 |
| KM-HN-1 |
| LAGE-1 |
| MAGE-A1 |
| MAGE-A2 |
| MAGE-A3 |
| MAGE-A4 |
| MAGE-A6 |
| MAGE-A9 |
| MAGE-A10 |
| MAGE-A12 |
| MAGE-C2 |
| mucin k |
| NA-88 |
| NY-ESO-1/LAGE-2 |
| SAGE |
| Sp17 |
| SSX-2 |
| SSX-4 |
| TRAG-3 |
| TRP2-INT2g |

b) Differentiation Antigens

| Gene/protein | Tumour |
|---|---|
| CEA | Intestinal carcinoma |
| gp100/Pmel17 | Melanoma |
| Kallikrein 4 | Prostate |
| mammaglobin-A | Breast cancer |
| Melan-A/MART-1 | Melanoma |
| NY-BR-1 | Breast cancer |
| OA1 | Melanoma |
| PSA | Prostate carcinoma |
| RAB38/NY-MEL-1 | Melanoma |
| TRP-1/gp75 | Melanoma |
| TRP-2 | Melanoma |
| tyrosinase | Melanoma |

c) Overexpressed Antigens

| Gene | Tissue expression |
|---|---|
| adipophilin | adipocytes, macrophages |
| AIM-2 | Ubiquitous (low level) |
| BING-4 | Ubiquitous (low level) |
| CPSF | Ubiquitous (low level) |
| cyclin D1 | Ubiquitous (low level) |
| Ep-CAM | Epithelial cells |
| EphA3 | Numerous |
| FGF5 | Brain, kidneys |
| G250/MN/CAIX | Stomach, liver, pancreas |
| HER-2/neu | Ubiquitous (low level) |
| IL13Ralpha2 | |
| Intestinal carboxyl esterase | liver, intestine, kidneys |
| alpha-foetoprotein | Liver |
| M-CSF | liver, kidneys |
| mdm-2 | ubiquitous (brain, muscle, lungs) |
| MMP-2 | Ubiquitous |
| MUC1 | Glandular epithelium |
| p53 | Ubiquitous (low level) |
| PBF | ovaries, pancreas, spleen, liver |
| PRAME | Testes, ovaries, endometrium, adrenal glands |
| PSMA | prostate, CNS, liver |

-continued

| Gene | Tissue expression |
|---|---|
| RAGE-1 | Retina |
| RNF43 | |
| RU2AS | testes, kidneys, bladder |
| secernin 1 | Ubiquitous |
| SOX10 | Ubiquitous (low level) |
| STEAP1 | Prostate |
| survivin | Ubiquitous |
| Telomerase | testes, thymus, bone marrow, lymph nodes |
| WT1 | testes, ovaries, bone marrow, spleen |
| BCLX (L) | Ubiquitous (low level) |
| DKK1 | Testes, prostate, mesenchymatous stem cells |
| ENAH (hMena) | Breast, prostate, colon-rectum stroma and epithelium, pancreas, endometrium |
| MCSP | Endothelial cells, chondrocytes, nonstriated muscle cells |
| RGS5 | Heart, skeletal muscle, pericytes |

Van der Bruggen et al. have produced a database referencing all human tumour antigens recognized by T lymphocytes and usable in cancer immunotherapy approaches according to the invention: http://www.cancerimmunity.org/peptidedatabase/Tcellepitopes.htm.

Other antigens may be used in the invention such as: Gastrin 17, Human Chorionic Gonadotropin, EGFRvIII, HER2, HER2/neu, P501, Guanylyl Cyclase C, PAP.

The word antigen encompasses antigens of natural or synthetic or artificial origin, antigens originating from the patient to be treated, antigenic fragments, derivatives or variants, so long as the antigen is able to inititiate the appropriate immune response. The antigens may be for example extracted, chemically synthesized or produced via genetic engineering.

In order to generate an effective immune response, dendritic cells have to be active and mature, they have to produce cytokines and chemokines and to express costimulation molecules that are necessary for the recruitment and activation of T lymphocytes.

Various types of adjuvants can be used to stimulate APCs, and in particular dendritic cells. Bacterial or viral RNA or DNA, heat shock proteins (HSPs), sugars, immune complexes and cytokines are various factors which induce APC maturation, and in particular dendritic cell maturation mediated by the stimulation of specific receptors (Toll-like receptor TLR, mannose receptor). Macrophages and dendritic cells do not all express the same receptors at their surface. The choice of the adjuvant therefore relates to a molecule capable of generating a cytotoxic immune response in humans and for which the receptor is found at the surface of the cells taking up the red blood cells of the invention, and therefore in particular at the surface of dendritic cells.

According to one embodiment, the adjuvant is a molecule encapsulated inside red blood cells or attached to the surface of red blood cells. These are preferably the red blood cells containing the antigen.

Alternatively, the adjuvant is encapsulated in, or attached to the surface of, other red blood cells treated separately. These red blood cells may also be modified or selected so as to promote phagocytosis thereof by APCs, in particular by dendritic cells. They may thus be, as previously described, in the form of an immune complex, or thermally or chemically modified, or else be xenogenic.

According to another embodiment, the adjuvant is a separate adjuvant composition, that can be administered simultaneously with or separately from the red blood cells containing the antigen.

It goes without saying that, as long as the adjuvant can be in a separate composition (red blood cell composition or adjuvant composition), the adjuvant can be administered concomitantly with the red blood cells containing the antigen, as a separate administration or in the form of a mixture, or administered separately, for example after the administration of the red blood cells comprising the antigen, in particular a few hours or days apart.

Among the adjuvants that can be used, mention may first and foremost be made of the preferred adjuvants below

- TLRs (Toll-like receptors) ligands, in particular imidazoquinolones, such as preferably: imidazoquinoline, e.g. imidazoquinoline CL097, imiquimod, resiquimod; CpG oligodeoxynucleotides; LPSs (lipopolysaccharides); poly(inosinic acid)-(polycytidylic acid poly(I:C));
- cytokines, in particular: interferon alpha, IL-2 (interleukin 2), IFNγ (interferon gamma), GM-CSF (Granulocyte Monocyte-Colony Stimulating Factor), IL-12 (interleukin 12), TNFα (Tumour Necrosis Factor alpha).

Among the other adjuvants that can be used, mention may in particular be made of:

- bacterial constituents, in particular BCG (*Bacillus* Calmette Guerin), MDP (Muramyl dipeptide), TDM (Trehalose dimycolate), LPS (lipopolysaccharide), MPL (monophosphoryl lipid A);
- mineral adjuvants, in particular: aluminium hydroxide, aluminium phosphate, potassium phosphate and calcium phosphate;
- bacterial toxins, in particular: CT (cholera toxin from *Vibrio cholera*), CTB (cholera toxin from *Vibrio cholera*), PT (pertussis toxin from *Bordetella pertussis*) LT (thermolabile lymphotoxin from *Escherichia coli*);
- KLH, Keyhole limpet haemocyanin.

Techniques for encapsulating active ingredients in red blood cells are known and the basic technique by lysis-resealing, which is preferred herein, is described in patents EP-A-101 341 and EP-A-679 101, to which those skilled in the art may refer. According to this technique, the primary compartment of a dialysis element (for example, dialysis tubing or a dialysis cartridge) is continuously fed with a suspension of red blood cells, while the secondary compartment contains an aqueous solution which is hypotonic with respect to the suspension of red blood cells, in order to lyse the red blood cells; next, in a resealing unit, the resealing of the red blood cells is induced in the presence of the tumour antigen by increasing the osmotic and/or oncotic pressure, and then a suspension of red blood cells containing the tumour antigen is collected.

Among the variants described up until now, preference is given to the method described in French Patent Application No. 0408667, which makes it possible to efficiently, reproducibly, safely and stably encapsulate the tumour antigen. This method comprises the following steps:

1—suspension of a red blood cell pellet in an isotonic solution at a haematocrit level greater than or equal to 65%, cooling between +1 and +8° C., 2—measurement of the osmotic fragility using a sample of red blood cells from said red blood cell pellet, it being possible for steps 1 and 2 to be carried out in any order (including in parallel), 3—lysis and internalization process of the tumour antigen, inside the same chamber, at a temperature constantly maintained between +1 and +8° C., comprising passing the suspension of red blood cells at a haematocrit level greater than or equal to 65%, and a hypotonic lysis solution cooled to between +1 and 8° C., through a dialysis cartridge; and the lysis parameters being adjusted according to the osmotic fragility previously measured; and 4—resealing process carried out in a second chamber, inside which the temperature is between +30 and +40° C., and in the presence of a hypertonic solution.

The "internalization" is intended to mean penetration of the tumour antigen inside the red blood cells.

In particular, for the dialysis, the red blood cell pellet is suspended in an isotonic solution at a high haematocrit level, greater than or equal to 65%, and preferably greater than or equal to 70%, and this suspension is cooled to between +1 and +8° C., preferably between +2 and 6° C., typically in the region of +4° C. According to a specific embodiment, the haematocrit level is between 65% and 80%, preferably between 70% and 80%.

The osmotic fragility is advantageously measured on the red blood cells just before the lysis step. The red blood cells or the suspension containing them are (is) advantageously at a temperature close to or identical to the temperature selected for the lysis. According to another advantageous feature of the invention, the osmotic fragility measurement is exploited rapidly, i.e. the lysis process is carried out shortly after the sample has been taken. Preferably, this period of time between taking the sample and beginning the lysis is less than or equal to 30 minutes, more preferably still less than or equal to 25, and even less than or equal to 20 minutes.

As regards the manner in which the lysis-resealing process is carried out, with the osmotic fragility being measured and taken into account, those skilled in the art may refer to French Patent Application No. 0408667 for further details.

According to one feature of the invention, the composition according to the invention comprises, at the end, a suspension of red blood cells at a haematocrit level of between about 40% and about 70%, preferably between about 45% and about 55%, better still about 50%. It is preferably packaged in a volume of about 10 to about 250 ml. The packaging is preferably in a blood bag of the type suitable for blood transfusion. The amount of encapsulated tumour antigen corresponding to the medical prescription is preferably entirely contained in the blood bag.

An object of the present invention is also a therapeutic anti-tumour vaccine comprising an effective amount of one or more compositions according to the invention. Thus, the vaccine may comprise a composition according to the invention, itself containing a population of red blood cells encapsulating one or more tumour antigens, in the presence or absence of encapsulated or nonencapsulated adjuvant, or at least two compositions according to the invention with different populations of red blood cells encapsulating one or more tumour antigens, in the presence of encapsulated or nonencapsulated adjuvant.

An object of the invention is also a method for inducing, in a patient, a cytotoxic cellular response against tumour cells or a tumour. This method comprises the administration to this patient of an effective amount of a composition according to the invention, in particular intravenously, by injection or infusion, preferably by infusion. This method is aimed in particular at inducing activation of the patient's dendritic cells and a $CD8^+$ cytotoxic cellular response. As described above, a specific $CD4^+$ helper and $CD8^+$ cytotoxic response is obtained.

An object of the invention is also an anticancer treatment method for inducing, in a patient, a cytotoxic cellular response as described above, against tumour cells or a tumour. This method comprises the administration to this patient of an effective amount of an anti-tumour vaccine according to the invention, in particular intravenously, by injection or infusion, preferably by infusion.

According to one feature of the invention, about 10 to about 250 ml of a suspension of red blood cells at a haematocrit level of between about 40% and about 70%, preferably between about 45% and about 55%, better still about 50%, are administered.

An object of the invention is also the use of a composition according to the invention, for the manufacture of a therapeutic anti-tumour, vaccine.

An object of the invention is also the use of a composition according to the invention, for inducing, in a host, a cytotoxic cellular response mediated by dendritic cells and directed against tumour cells or a tumour.

Another object of the invention is a composition according to the invention, for use as a therapeutic anti-tumour vaccine.

The present invention will now be described in greater detail by means of embodiments taken by way of nonlimiting examples, and which refer to the attached drawings.

EXAMPLES

Example 1. Method for Encapsulating Ovalbumin in Murine and Human Red Blood Cells and in Porcine Red Blood Cells Variant 1:

Ovalbumin (protein of 45 kDa, hen egg ovalbumin) is encapsulated in murine red blood cells (OF1 mice or C57Bl/6 mice) by the method of hypotonic dialysis in dialysis tubing. The red blood cell suspension is washed several times before being brought to a haematocrit of 70% for the dialysis. The dialysis is carried out in dialysis tubing in a lysis buffer of low osmolarity for about 1 hour or 30 min when the dialysis occurs after a heat treatment. The red blood cells are then resealed by means of a solution of high osmolarity for 30 minutes. After a few washes, the final product is taken up in a buffer, Sag-mannitol, and haematocrit is brought to 50%.

Variant 2 for Example 1:

Ovalbumin is herein encapsulated in the murine red blood cells by the method of hypotonic dialysis in a dialysis column. The red blood cell suspension is washed several times before being brought to a haematocrit of 70% for the dialysis. The dialysis is carried out in a dialysis column in a lysis buffer of low osmolarity for about 10 min. As soon as they leave the column, the red blood cells are resealed by means of a solution of high osmolarity for 30 minutes at 37° C. After a few washes, the final product is taken up in a NaCl glucose buffer containing glucose SAG mannitol, or decomplemented plasma, and haematocrit is brought back to 50%.

Example 2. Heat Treatment on the Red Blood Cells

When the encapsulation is realized according to variant 1 of example 1, heat treatment is realized before dialysis process. When encapsulation is realized according to variant 2 of example 1, heat treatment is realized after the dialysis and resealing process and before washing steps and addition of NaCl glucose buffer.

The red blood cells are washed several times before being brought to a haematocrit of 10%. They are then heated for 30 minutes at 48° C.

Example 3. Antibody Treatment on the Red Blood Cells Containing Ovalbumin

The suspension of red blood cells encapsulating ovalbumin is washed several times before being brought to $10^9$ cells/ml for the in vivo test and $10^8$ cell/ml for the in vitro test. It is incubated with the anti-TER119 antibody (10 μg/ml for the in vitro test and 23 μg/ml or 5 μg/ml for the in vivo test) for 30 minutes at 4° C. After a few washes, the final product is taken up in a buffer with injectable qualities, and haematocrit is brought to 50%.

Example 4. Chemical Treatment with Bis(Sulphosuccinimidyl) Suberate (BS3) on the Red Blood Cells Containing Ovalbumin The suspension of red blood cells encapsulating ovalbumin is washed several times before being brought to $1.7\times10^6$ cell/μl with PBS and mixed with one volume of a buffer solution of 2 mM BS3 (the BS3 solution contains glucose and phosphate buffer, pH 7.4), so as to obtain a final BS3 concentration of 1 mM. The cells are incubated for 30 minutes at room temperature. The reaction is quenched by adding one volume of 20 mM Tris-HCl. After incubation at room temperature for 5 minutes, the mixture is centrifuged at 800 g for 5 min, 4° C. The cells are then washed twice with PBS containing glucose (centrifugation at 800 g) and once with SAG-mannitol (centrifugation at 1000 g) for 10 min, before constituting the final products.

Example 5. Measurement of the Phagocytosis of Ovalbumin-Containing Red Blood Cells by Dendritic Cells In Vitro The effect of the various treatments (heat and antibody) on the phagocytosis efficiency of the red blood cells obtained according to variant 1 of example 1, by dendritic cells, is measured in vitro. The red blood cells are labelled with a fluorescent label, CFSE (carboxyfluorescein succinimidyl ester), for 20 min at 4° C. CFSE is a non-fluorescent dye which diffuses through the cell membrane. Once inside the cell, the molecule becomes fluorescent subsequent to its cleavage by intracellular esterases.

Dendritic cells are isolated from the spleen of C57Bl/6 mice using magnetic beads. These beads carry antibodies which recognize the CD11c marker, thereby making it possible to isolate the $CD11c^+$ dendritic cell fraction.

The CFSE-labelled or unlabelled red blood cells are then incubated with the dendritic cells ($10\times10^6$ cell/ml) at a ratio of 20:1 in a final volume of 200 μl/well of round-bottomed 96-well culture plates for 4 hours at 37° C. and 5% $CO_2$. After culturing for 4 hours, the red blood cells not ingested by the dendritic cells are lysed with $NH_4Cl$, and several washes are carried out. The capture of the CFSE fluorochrome by the dendritic cells is then measured by flow cytometry (R. Segura et al., J. Immunol, January 2006, 176(1): 441-50).

Three populations of red blood cells were tested:

(A) red blood cells loaded with ovalbumin and not labelled with the CFSE fluorochrome, (B) red blood cells loaded with ovalbumin and labelled with CFSE, (C) red blood cells loaded with ovalbumin, treated with the anti-TER 119 antibody and labelled with CFSE.

Results

TABLE 1

| Percentage of dendritic cells having phagocytosed fluorescent red blood cells: | |
|---|---|
| Red blood cell population | % of dendritic cells |
| (A) | 4% |
| (B) | 27% |
| (C) | 36% |

The murine red blood cells loaded with ovalbumin and treated with the anti-TER 119 antibody were more efficiently phagocytosed by the dendritic cells isolated from the spleen than the untreated red blood cells in vitro, after 4 hours of coculture (FIG. 1, respectively C and B). 36% of the dendritic cells phagocytosed the red blood cells carrying the antibody, against only 27% in the absence of antibody. Phagocytosis of the antibody-treated red blood cells by a population not expressing the CD11c dendritic cell marker was also observed (10.9%; FIG. 1, C).

Example 6. Measurement of the Phagocytosis of Red Blood Cells Containing Ovalbumin, by Macrophages and Dendritic Cells of the Spleen and Liver In Vivo on Mice This study is an allogenic study since OF1 mice red blood cells containing ovalbumin are injected to not consanguineous C57Bl/6 mice.

Three batches of $74\times10^7$ red blood cells, from OF1 mice, loaded with ovalbumin (variant 1 of example 1) heat treated, treated with the anti-TER 119 antibody (as described in examples 2 and 3, respectively) or not treated are prepared. These batches are divided up in the following way:

Batch 1: no heat or antibody treatment (FIGS. 2, A and D)

Batch 2: heat treated (FIGS. 2, B and E)

Batch 3: treated with the anti-TER 119 antibody (FIGS. 2, C and F).

Each batch is labelled with CFSE and injected intravenously into C57Bl/6 mice. Three hours after the injection, the blood, the spleen and the liver of the mice are taken. The percentage of fluorescent red blood cells circulating in the blood of the mice is measured by flow cytometry. The fluorescence incorporated into the spleen macrophages expressing the F4/80 marker (FIG. 2, A, B, C), into the liver macrophages expressing the F4/80 marker and into the spleen dendritic cells expressing the CD11c marker (FIG. 2, D, E, F) is measured by flow cytometry.

Results

TABLE 2

| Percentage of macrophages or dendritic cells from the spleen, having phagocytosed fluorescent red blood cells 3 hours after injection into the mouse: | | |
|---|---|---|
| Batches | Macrophages | Dendritic cells |
| 1 | 28% | 5% |
| 2 | 68% | 19% |
| 3 | 81% | 22% |

3 hours after injection, the murine red blood cells loaded with ovalbumin and heat-treated or treated with the anti-TER 119 antibody are almost no longer present in the blood of the mouse (1.6% and 1%), whereas there are still untreated, ovalbumin-loaded red blood cells in the blood of the mouse (4.6%).

The red blood cells that have been heat-treated or treated with the anti-TER 119 antibody are phagocytosed by the F4/80 macrophages and CD11c dendritic cells of the spleen (FIG. 2).

The red blood cells treated with the anti-TER 119 antibody were more efficiently phagocytosed by the F4/80 macrophages of the spleen than the heat-treated red blood cells or the untreated red blood cells (FIG. 2, A, B, C). 81% of the spleen macrophages phagocytosed the antibody-treated red blood cells, against 68% of macrophages having phagocytosed the heat-treated red blood cells and only 28% in the untreated batch (Table 2).

The heat-treated or antibody-treated red blood cells were also more efficiently phagocytosed by the CD11c dendritic cells from the spleen than the untreated red blood cells (FIG. 2). Respectively 22% and 19% of dendritic cells phagocytosed the antibody-treated red blood cells and the heat-treated red blood cells, against only 5% in the case of the untreated red blood cells (Table 2).

Phagocytosis of the antibody-treated red blood cells by a population from the spleen not expressing the CD11c dendritic cell marker or the F4/80 macrophage marker was also observed (11.9% and 12.8%, FIG. 2).

TABLE 3

Percentage of liver macrophages having phagocytosed fluorescent red blood cells 3 hours after injection into the mouse.

| Batches | Macrophages |
|---|---|
| 1 | 24% |
| 2 | 40% |
| 3 | 50% |

The heat-treated red blood cells or the red blood cells treated with the anti-TER 119 antibody are phagocytosed by the F4/80 macrophages of the liver.

The red blood cells treated with the anti-TER 119 antibody were more efficiently phagocytosed by the F4/80 macrophages of the liver than the heat-treated red blood cells or than the untreated red blood cells. 50% of the liver macrophages phagocytosed the antibody-treated red blood cells, against 40% of macrophages having phagocytosed the heat-treated red blood cells and only 24% in the untreated batch (table 3).

In conclusion, the binding of the antibody to the red blood cells and the heat treatment allowed efficient targeting of the red blood cells in the spleen and the liver, and a significant increase in the percentage of dendritic cells and of macrophages capable of phagocytizing these red blood cells.

Example 7. Measurement of the Phagocytosis of Mouse Red Blood Cells Containing Fluorescent Ovalbumin by Bone Marrow Macrophages and Dendritic Cells In Vivo This study is an autologous study, since OF1 mouse red blood cells are injected into OF1 mice.

Four batches of $132\times10^7$ OF1 mouse red blood cells loaded with fluorescent ovalbumin (Serlabo Technologies, ref WO-LS003054) prepared using variant 2 of example 1 and treated with the anti-TER 119 antibody, with heat or with BS3 (as described in Examples 3, 2 and 4, respectively) or not treated are prepared. Each batch of red blood cells is injected intravenously into two mice. One and a half hours after the injection, the mice are sacrificed and the femurs of the mice are removed. The fluorescence incorporated into the macrophages expressing the F4/80 marker or the CD11b marker, the granulocytes expressing the Gr1 marker, the myeloid dendritic cells expressing the CD11c and CD11b markers and into the plasmacytoid dendritic cells expressing the CD11c and CD8 markers is measured by flow cytometry.

Batch 1: ovalbumin-loaded red blood cells, treated with BS3

Batch 2: ovalbumin-loaded red blood cells, heat-treated

Batch 3: ovalbumin-loaded red blood cells, treated with the anti-TER 119 antibody Batch 4: ovalbumin-loaded red blood cells Batch 5: NaCl glucose Results

TABLE 4

Percentage of bone marrow macrophages, granulocytes or dendritic cells having phagocytosed fluorescent ovalbumin 1 hour 30 min after the injection:

| Batches | F4/80 macro-phages | CD11b macro-phages | Granulo-cytes | Myeloid dendritic cells | Plasma-cytoid dendritic cells |
|---|---|---|---|---|---|
| 1 | 2.5 | 0.05 | 12.5 | 2.7 | 2.4 |
| 2 | 3.3 | 0 | 15.5 | 2.2 | 3.4 |
| 3 | 17.7 | 1.75 | 21 | 15.3 | 6 |
| 4 | 2.4 | 0 | 13 | 1.6 | 2.4 |
| 5 | 0.5 | 0.1 | 1.3 | 0.8 | 1.5 |

One and a half hours after injection, the ovalbumin-loaded red blood cells treated with the anti-TER 119 antibody were efficiently phagocytosed by the F4/80 macrophages, the granulocytes and the dendritic cells of the bone marrow. The myeloid dendritic cells of the bone marrow are the cells most involved in the phagocytosis of the ovalbumin-loaded red blood cells treated with the anti-TER 119 antibody.

In conclusion, the use of red blood cells treated with the anti-TER 119 antibody allows the best targeting and phagocytosis of the red blood cells by immune cells in the bone marrow.

Example 8. Measurement of the Ovalbumin-Specific CD4 T Cell Response after a Single Injection of Ovalbumin-Loaded Red Blood Cells and of Poly(I:C) Adjuvant The evaluation of the OVA (ovalbumin)-specific CD4 T cell response consists in measuring the percentage of OVA-specific CD4 T cells, the proliferation of these cells, the level of activation of these cells and the production of IFNg (g=gamma).

The evaluation of the CD4 T cell response is realized using an adaptation of the methods described in Russo V. et al. The Journal of Clinical Investigation, 2007, 117: 3087-3096; Stoitzner P, et al., The Journal of Immunology 2008, 180: 1991-1998. The CD4 T cells of OT-11 transgenic mice (Charles River, ref C57BL/6-Tg(TcraTcrb425Cbn/Crl)) are used to measure the OVA-specific CD4 T cell response. The OT-II mice are mice expressing only CD4 T cells which recognize the ovalbumin peptide 323-339 associated with major histocompatibility complex class II molecules.

The OT-II transgenic CD4 T cells are isolated from the spleen of OT-II mice and labelled with CFSE, before being injected intravenously into Ly5.1 mice. OT-11 mice and Ly5.1 mice have the same genetic background, but the cells of both types of mice can be identified by means of the CD45 marker. This is because the cells of OT-II mice express the CD45.2 marker, whereas the Ly5.1 mice express the CD45.1 marker.

20 hours after the injection of the transgenic mouse CD4 T cells, the Ly5.1 mice receive an intravenous injection of the following batches. Three mice are injected with the batches containing red blood cells and two mice are injected with the batches containing free OVA or the control.

Two batches of $183\times10^7$ red blood cells of C57Bl/6 mice loaded with ovalbumin (Serlabo Technologies, ref WO-LS003054) prepared using variant 2 of example 1 and treated or not with the anti-TER 119 antibody (as described in example 3) are prepared. The adjuvant, Poly (I:C) (Invivogen, ref tlrl-pic), is added to these batches, as well as to the batch containing free ovalbumin. The amount of Poly (I:C) injected per mouse is 25 μg. The amount of OVA injected into the mice is indicated in Table 5.

This is an autogenic study since ovalbumine-loaded C57Bl/6 mice red blood cells are injected to Ly5.1 mice. C57Bl/6, Ly5.1 and OT-II mice have the same genetic background.

Batch 1: Poly (I:C) and ovalbumin-loaded red blood cells treated with the anti-TER 119 antibody
Batch 2: Poly (I:C) and ovalbumin-loaded red blood cells
Batch 3: Poly (I:C) and free ovalbumin
Batch 4: Plasma Three days after the injection of the batches, the mice are sacrificed and the spleens of the mice are removed. The percentage of OVA-specific CD4 T cells in the spleen of the mice is measured by flow cytometry using the CD4 and CD45.2 markers (Table 5). The number of OVA-specific CD4 T cells is calculated from the percentage of OVA-specific CD4 T cells and the number of total lymphocytes counted with trypan blue (Invitrogen, ref 15250061) (Table 5).

The proliferation and the activation of the OVA-specific CD4 T cells in the spleen of the mice is measured by flow cytometry using the CD4, CD44 and CD45.2 markers and using CFSE (Tables 6 and 7). At each cell division, the amount of CFSE contained in the OVA-specific CD4 T cells is divided by a factor of 2, which makes it possible to determine the number of cell divisions by flow cytometry (FIG. 3).

The production of IFNg by the mice splenocytes is measured in the culture supernatants after 3 days of in vitro stimulation in the presence of 10 μg/ml of ovalbumin peptide 323-339 (Neomps, ref) by means of an ELISA assay.

Results

TABLE 5

Percentage and number of OVA-specific CD4 T cells three days after injection of the batches (mean ± standard deviation):

| Batches | Amount of OVA injected into the mice (μg) | % of OVA-specific CD4 T cells | Number of OVA-specific CD4 T cells (millions of cells) |
|---|---|---|---|
| 1 | 160 | 6.6 ± 1.4* | 8 ± 2* |
| 2 | 129 | 3.6 ± 0.9** | 4.1 ± 2* |
| 3 | 150 | 0.8 ± 0.3 | 1.3 ± 0.7 |
| 4 | 0 | 0.1 ± 0.1 | 0.2 ± 0.1 |

Three days after injection of the batches, the mice injected with Poly (I:C) and ovalbumin-loaded red blood cells treated or not with the anti-TER 119 antibody have a significantly higher percentage and number of OVA-specific CD4 T cells than the mice injected with free OVA and Poly (I:C) (Student test *p=0.01, **p=0.02).

Furthermore, the batch containing ovalbumin-loaded red blood cells treated with the anti-TER 119 antibody is more effective in inducing an increase in the number of OVA-specific CD4 T cells than the batch containing untreated, ovalbumin-loaded red blood cells (Student test p=0.04).

TABLE 6

Percentage of OVA-specific CD4 T cells which have divided 0, 1, 2, 3, 4, 5, 6 or 7 times three days after injection of the batches:

| Batches | % of OVA-specific CD4 T cells at each division cycle (mean ± standard deviation) | | | | | | | |
|---|---|---|---|---|---|---|---|---|
| | 0 | 1 | 2 | 3 | 4 | 5 | 6 | 7 |
| 1 | 0 ± 0 | 0 ± 0 | 0.1 ± 0 | 0.3 ± 0 | 1.7 ± 0 | 9.4 ± 0.1 | 35.9 ± 0.3 | 52.5 ± 0.2 |
| 2 | 0.1 ± 0 | 0.1 ± 0 | 0.2 ± 0 | 0.8 ± 0.1 | 4.2 ± 0.8 | 19.2 ± 3.2 | 43.7 ± 2.2 | 31.5 ± 6.3 |
| 3 | 1.9 ± 1.4 | 6.9 ± 5.2 | 15.6 ± 9.5 | 18.7 ± 5.6 | 19.7 ± 0.4 | 16.4 ± 5.3 | 13.9 ± 10.1 | 6.8 ± 5.9 |
| 4 | 69.7 ± 4.9 | 1.3 ± 1 | 0.1 ± 0.2 | 0.3 ± 0.4 | 5.6 ± 3.7 | 3.7 ± 1.1 | 5.3 ± 2.8 | 13.6 ± 2.5 |

These observations are confirmed by the in vivo cell proliferation results (Table 6 and FIG. 3). Cell division induces a decrease of the CFSE fluorescence intensity: disparition of half of the fluorescent material at each division (FIG. 3A). The OVA-specific CD4 T cells divide more rapidly (Table 6 and FIG. 3A) for the mice injected with Poly (I:C) and ovalbumin-loaded red blood cells treated with the anti-TER 119 antibody (6 to 7 divisions) in comparison with the mice injected with free OVA and Poly (I:C) (3 to 4 divisions). Furthermore, the batch containing ovalbumin-loaded red blood cells treated with the anti-TER 119 antibody appears to be more effective in inducing cell proliferation than the batch containing untreated, ovalbumin-loaded red blood cells.

TABLE 7

Level of activation of OVA-specific CD4 T cells three days after injection of the batches:

| Batches | Mean of OVA-specific CD4 T cells activation fluorescence (mean ± standard deviation) |
|---|---|
| 1 | 32.6 ± 2.3 |
| 2 | 37.6 ± 3.5 |
| 3 | 34.6 ± 3.9 |
| 4 | 11.4 ± 0.5 |

The results of the cell activation level (characterized by the level of expression of the CD44 marker) show that all the dividing OVA-specific CD4 T cells have a high cell activation level (Table 7 and FIG. 3). In addition, the activation level of the OVA specific CD4 T cells can be correlated to the number of divisions of these cells: the more the cells have divided and have lost their CFSE marker content, the more they express a high level of activation marker (FIG. 3B).

TABLE 8

| Production of IFNg by splenocytes stimulated in vitro with 10 μg/ml of ovalbumin peptide 323-339 for 3 days: | |
|---|---|
| Batches | Production of IFNg by splenocytes in ng/ml (mean ± standard deviation) |
| 1 | 56.3 |
| 2 | 60 ± 26.8 |
| 3 | 9.4 ± 1.6 |
| 4 | 6.7 ± 1 |

The results of IFNg production by splenocytes show a strong production of IFNg by the splenocytes of mice injected with Poly (I:C) and ovalbumin-loaded red blood cells treated or not treated with the anti-TER119 antibody.

In conclusion, these results demonstrate the superiority of the ovalbumin-loaded red blood cells treated or not with the anti-TER 119 antibody, on the activation and proliferation of OVA-specific CD4 T cells capable of producing IFNg.

Example 9. Measurement of the Ovalbumin-Specific CD8 T Cell Response after a Single Injection of Ovalbumin-Loaded Red Blood Cells and of Poly (I:C) Adjuvant The evaluation of the OVA-specific CD8 T cell response consists in measuring the percentage of OVA-specific CD8 T cells, the production of IFNg and the cell lysis, in vivo, of the cells presenting the ovalbumin peptide 257-264 associated with major histocompatibility complex class I molecules.

This study is an allogenic study, since ovalbumin-loaded red blood cells from OF1 mice are injected into not consanguineous C57Bl/6 mice.

Two batches of $167\times10^7$ ovalbumin-loaded OF1 mouse red blood cells prepared using variant 2 of example 1 and treated or not with the anti-TER 119 antibody (as described in example 3) are prepared. The adjuvant, Poly (I:C), is added to these batches, and also to the batch containing free ovalbumin. The amount of Poly (I:C) injected per mouse is 25 μg. The amount of OVA injected into the mice is indicated in Table 9.

The batches are injected intravenously into C57Bl/6 mice. A minimum of 4 mice are injected with a given batch. In vivo cell lysis is measured using an adaptation of the method described by Hervas-Stubbs S. et al., Blood 2007, 109: 5318-5326. Cells presenting the ovalbumin peptide 257-264 associated with major histocompatibility complex class I molecules are injected into the immunized mice. Briefly, six days after the injection, the mice receive an injection of $0.5\times10^6$ splenocytes presenting the ovalbumin 257-264 peptide (Neomps, ref SC1302) and labelled with a moderate concentration of CFSE, and of $0.5\times10^6$ splenocytes not presenting the peptide and labelled with high concentrations of CFSE (cell lysis control).

Latex beads coupled to ovalbumine peptide 257-264 (BOVAp) and poly(I:C) are used as positive control to induce a CD8 T immune response against ovalbumine. It has been shown that the injection of BOVAp and of poly(I:C) induces an increase of the percentage of ovalbumine-specific CD8 T cells and the destruction of cells presenting the OVA257-264 peptide in vivo (Herva-Stubbs).

Batch 1: Poly (I:C) and ovalbumin-loaded red blood cells treated with the anti-TER 119 antibody Batch 2: Poly (I:C) and ovalbumin-loaded red blood cells Batch 3: Latex beads coupled to the ovalbumin peptide 257-264

Batch 4: Poly (I:C) and latex beads coupled to the ovalbumin peptide 257-264

Batch 5: Poly (I:C) and free ovalbumin

Batch 6: NaCl glucose+plasma 16 hours after injection of the splenocytes, the mice are sacrificed by euthanasia and the spleens of the mice are removed. The percentage of OVA-specific CD8 T cells in the spleen of the mice is measured by flow cytometry using tetramer and the CD8 marker (Table 9). IFNg production and expression of the marker associated with degranulation (CD107) by CD8 T cells was measured by flow cytometry after in vitro stimulation for 4 hours in the presence of 0.1 μg/ml of ovalbumin peptide 257-264 (Table 10). In vivo cell lysis was measured by flow cytometry using CFSE (Table 11).

Results

TABLE 9

| Percentage of OVA-specific CD8 T cells seven days after injection of batches (mean ± standard deviation): | | | |
|---|---|---|---|
| Batch | Quantity of OVA injected into mice (μg) | % of OVA-specific CD8 T cells (mean ± standard deviation) | % of OVA-non-specific T cells (mean ± standard deviation) |
| 1 | 95 | 14 ± 3.2* | 2.4 ± 0.2 |
| 2 | 91 | 12.5 ± 5.2** | 1.2 ± 0.5 |
| 3 | 0 | 1.2 ± 0.1 | 1.2 ± 0.1 |
| 4 | 0 | 2.5 ± 0.4* | 0.9 ± 0.1 |
| 5 | 130 | 2.4 ± 1.4 | 1 ± 0.2 |
| 6 | 0 | 0.7 ± 0.4 | 1 ± 0.1 |

Mice injected with Poly(I:C) and ovalbumin-charged red blood cells which had either been treated or had not been treated with anti-TER119 antibody have a significantly higher percentage of OVA-specific CD8 T cells than mice injected with free OVA and Poly(I:C) or mice injected with Poly(I:C) and BOVAp (Student's test: *p=0.001 and **p=0.01).

TABLE 10

| Production of IFNg by CD8 T cells stimulated in vitro with 0.1 μg/ml of ovalbumin peptide 257-264 for 4 hours: | | |
|---|---|---|
| Batch | % CD8 T cells producing IFNg | % of CD8 T cells producing IFNg and expressing CD107 marker |
| 1 | 8.7 ± 1.8* | 71 ± 4* |
| 2 | 6.6 ± 1.7* | 71 ± 4* |
| 3 | 1.4 ± 0.1 | 33 ± 4.5 |
| 4 | 2.8 ± 0.5 | 57 ± 5.5 |
| 5 | 1.8 ± 0.5 | 46 ± 7 |
| 6 | 0.7 ± 0.1 | 18 ± 2 |

The CD8 T cells generated are effective and cytotoxic since they produce IFNg and express the CD107 marker in response to stimulation with the ovalbumin peptide (Table 10). The percentage of CD8 T cells producing IFNg and expressing CD107 is significantly higher for mice injected with Poly(I:C) and ovalbumin-charged red blood cells which had either been treated or had not been treated with anti-TER119 antibody than for mice injected with free OVA and Poly(I:C) or Poly(I:C) and BOVAp (Student's test, p<0.008).

TABLE 11

| Percentage of in vivo anti-OVA-specific cell lysis (mean ± standard deviation): | |
|---|---|
| Batch | % cell lysis, in vivo (mean ± standard deviation) |
| 1 | 82 ± 7 |
| 2 | 83 ± 4 |
| 5 | 53 ± 8 |
| 6 | 0 |

The cell lysis results correlate with expression of the marker associated with degranulation (Tables 10 and 11). Injection of Poly(I:C) and ovalbumin-charged red blood cells which had either been treated or had not been treated with anti-TER119 antibody induced lysis of cells displaying ovalbumin peptide 257-264 in a manner which was more effective than injection of Poly(I:C) and free ovalbumin (Table 10).

In conclusion, these results demonstrate the superiority of ovalbumin-charged red blood cells which have either been treated or have not been treated with anti-TER119 antibody in the activation and proliferation of cytotoxic CD8 T cells capable of producing IFNg, degranulating and lysing cells displaying ovalbumin peptide 257-264.

Example 10. Measuring the Maintenance of the Ovalbumin-Specific CD8 T Cell Response 30 Days after a Single Injection of Ovalbumin-Charged Red Blood Cells and Adjuvant Poly(I:C)

Evaluating the maintenance of the OVA-specific CD8 T cell response consisted of measuring the percentage of OVA-specific CD8 T cells and cell lysis in vivo 34 days after a single injection.

This study was an allogenic study, since red blood cells charged with OF1 mouse ovalbumin were injected into non-consanguineous C57Bl/6 mice.

Two batches were prepared of $150\times10^7$ of ovalbumin-charged OF1 mouse red blood cells obtained in accordance with variant 2 of Example 1 which had or had not been treated with anti-TER119 antibody (as described in Example 3). The adjuvant, Poly(I:C), was added to these batches, and also to the batch containing free ovalbumin or BOVAps. The quantity of Poly(I:C) injected per mouse was 25 μg. The quantity of OVA injected into the mice is shown in Table 12.

The batches were injected intravenously into C57Bl/6 mice. Three mice were injected with a given batch. To measure cell lysis in vivo, cells displaying ovalbumin peptide 257-264 associated with molecules of the major histocompatibility complex of class I were injected into immunized mice. 33 days after injection, the mice received an injection of $0.5\times10^6$ splenocytes displaying ovalbumin peptide 257-264 (NeoMPS, reference SC1302) and labelled with a moderate concentration of CFSE and of $0.5\times10^6$ splenocytes not displaying the peptide and labelled with a high concentration of CFSE (cell lysis assay).

Batch 1: Poly(I:C) and ovalbumin-charged red blood cells, treated with anti-TER119 antibody Batch 2: Poly(I:C) and ovalbumin-charged red blood cells Batch 3: Latex beads coupled with ovalbumin peptide 257-264: BOVAp Batch 4: Poly(I:C) and BOVAp Batch 5: Poly(I:C) and free ovalbumin Batch 6: NaCl glucosated+plasma 16 hours after injecting the splenocytes, the mice were euthanized and their spleens were removed. The percentage of OVA-specific CD8 T cells in the spleens of the mice was measured by flow cytometry using tetramer and CD8 marker (Table 12). In vivo cell lysis was measured by flow cytometry using CFSE (Table 13).

TABLE 12

| Percentage of OVA-specific CD8 T cells 34 days after injection of batches (mean ± standard deviation) | | |
|---|---|---|
| Batch | Quantity of OVA injected into mice (μg) | % of OVA-specific CD8 T cells (mean ± standard deviation) |
| 1 | 170 | 1.5 ± 0.2 |
| 2 | 138 | 1.7 ± 0.3 |
| 3 | 0 | 1.6 ± 0.1 |
| 4 | 0 | 1.4 ± 0.1 |
| 5 | 150 | 2.2 ± 0.2 |
| 6 | 0 | 1.8 ± 0.06 |

34 days after injection, the percentage of OVA-specific CD8 T cells was equivalent for each group (Table 12). This result is not surprising given that the peak CD8 T cell proliferation was at about day 7 and it was followed by a contraction phase (Hervas-Stubbs S et al, Blood, 2007, 109: 5318-5326).

TABLE 13

| Percentage of anti-OVA-specific cell lysis in vivo (mean ± standard deviation): | |
|---|---|
| Batch | % cell lysis in vivo (mean ± standard deviation) |
| 1 | 49 ± 9* |
| 2 | 54 ± 28 |
| 3 | 12 ± 5.4 |
| 4 | 21.6 ± 12 |
| 5 | 20.4 ± 19 |
| 6 | 0.9 ± 0.9 |

34 days after injection, the OVA-specific CD8 T cells were still capable of lysing cells displaying ovalbumin peptide 257-264 (Table 13). Injection of Poly(I:C) and ovalbumin-charged red blood cells treated with anti-TER119 antibody induced cell lysis in a manner which was more effective than injection of Poly(I:C) and BOVAp (*Student's test, p<0.04).

In conclusion, these results demonstrate that ovalbumin-charged red blood cells are superior not only as regards activation and proliferation of cytotoxic CD8 T cells, but also as regards maintenance/survival of these T cells which are capable of lysing cells displaying ovalbumin peptide 257-264.

Example 11. Measurement of the Ovalbumin-Specific CD8 T Cell Response after a Single Injection of Chemically Treated, Ovalbumin-Loaded Red Blood Cells and of Poly (I:C) Adjuvant This study is an allogenic study, since ovalbumin-loaded red blood cells from OF1 mice are injected into not consanguineous C57Bl/6 mice.

A batch of $132 \times 10^7$ ovalbumin-loaded OF1 mouse red blood cells prepared using variant 2 of example 1 and chemically treated with 1 mM BS3 (as described in example 4) is prepared. The adjuvant Poly (I:C), is added to this batch, and to the batch containing free ovalbumin. The amount of Poly (I:C) injected per mouse is 25 μg. The amount of OVA injected into the mice is indicated in Table 14.

Batch 1: Poly (I:C) and ovalbumin-loaded red blood cells treated with 1 mM BS3

Batch 2: Poly (I:C) and free ovalbumin

Batch 3: Poly (I:C)

Batch 4: NaCl containing glucose

The batches are injected intravenously into C57Bl/6 mice. A minimum of 3 mice are injected with a given batch. Seven days after the injection, the mice are sacrificed and the spleens of the mice are removed. The percentage of OVA-specific CD8 T cells in the spleen of the mice is measured by flow cytometry using tetramer and the CD8 marker (Table 14).

Results

TABLE 14

Percentage and number of OVA-specific CD8 T cells seven days after injection of the batches (mean ± standard deviation):

| Batches | Amount of OVA injected into the mice (μg) | % of OVA-specific CD8 T cells (mean ± standard deviation) |
|---|---|---|
| 1 | 38 | 1.8 ± 0.6 |
| 2 | 150 | 1.2 ± 0.3 |
| 3 | 0 | 1 ± 0 |
| 4 | 0 | 0.8 ± 0.1 |

The mice injected with Poly (I:C) and ovalbumin-loaded red blood cells treated with BS3 have a higher percentage of OVA-specific CD8 T cells than the mice injected with free OVA and Poly (I:C) or than the mice injected with Poly (I:C). These results are not statistically different, but it should be noted that the amount of free OVA injected is more than three times greater than the amount of OVA injected in the batch containing the OVA-loaded red blood cells.

In conclusion, these results show that the ovalbumin-loaded red blood cells treated with BS3 are also capable of generating OVA-specific CD8 T cells.

Example 12. Measurement of the Ovalbumin-Specific CD8 T Cell Response after a Single Injection of Ovalbumin-Loaded Red Blood Cells and of CL-097 Adjuvant This study is an allogenic study, since ovalbumin-loaded red blood cells from OF1 mice are injected into not consanguineous C57Bl/6 mice.

Batches of $119 \times 10^7$ ovalbumin-loaded OF1 mouse red blood cells prepared using variant 1 of example 1 and treated or not with the anti-TER 119 antibody (as described in example 3) are prepared. The adjuvant, CL097 (Invivogen, ref tlrl-c97), is or is not added to these batches. The amount of CL097 injected per mouse is 0.15 μg. The amount of OVA injected into the mice is indicated in Table 15.

Batch 1: CL097 and ovalbumin-loaded red blood cells treated with the anti-TER 119 antibody Batch 2: ovalbumin-loaded red blood cells treated with the anti-TER 119 antibody Batch 3: CL097 and ovalbumin-loaded red blood cells Batch 4: ovalbumin-loaded red blood cells Batch 5: NaCl containing glucose The batches are injected intravenously into C57Bl/6 mice. Four days after the injection, the mice are sacrificed and the spleens of the mice are removed. The IFNg production by the splenocytes of mice injected with the various batches is measured in the culture supernatants after three days of in vitro stimulation in the presence of 0.1 μg/ml of ovalbumin peptide 257-264 by means of ELISA assay.

Results

TABLE 15

IFNg production by splenocytes stimulated in vitro with 0.1 μg/ml of ovalbumin peptide 257-264 for 3 days:

| Batches | Amount of OVA injected into the mice (μg) | IFNg production by splenocytes in ng/ml |
|---|---|---|
| 1 | 83 | 15.2 |
| 2 | 83 | 5.7 |
| 3 | 103 | 11.4 |
| 4 | 103 | 7.4 |
| 5 | 0 | 0.4 |

The results of IFNg production by the splenocytes show a greater IFNg production when the mice received an injection of both the CL097 adjuvant and ovalbumin-loaded red blood cells treated or not with the anti-TER 119 antibody.

In conclusion the CL097 adjuvant also potentiates the IFNg response induced by the injection of the ovalbumin-loaded red blood cells.

Example 13. Measure of Tumoral Growth after One Injection of Adjuvant Poly (I:C) and Treated or Untreated Ovalbumin-Loaded Erythrocytes in Mice The purpose of this study is to measure the tumor growth of EG.7 cell line in C57Bl/6 mice after injection of a single dose of Poly (I:C) and treated or untreated ovalbumin-loaded erythrocytes. EG.7 tumor cells are obtained from ATCC (ATCC-CRL-2113). EG.7 cells originate from the EL.4 cell line, which synthesize and secrete OVA constitutively.

This is an allogenic study since ovalbumin-loaded erythrocytes from OF1 mice are injected into C57Bl/6 mice. The model in this experiment is a prophylactic model.

Two batches of $165 \times 10^7$ antibody-treated or untreated ovalbumin-loaded erythrocytes from OF1 mice are prepared according to variant 2 of example 1. The adjuvant, Poly (I: C), is added to those batches. 25 μg of Poly (I: C) is injected per mice. The negative control is a suspension of unloaded erythrocytes. OVA amounts injected to mice are indicated in table 16.

Batch 1: Poly (I: C) and antibody-treated ovalbumin-loaded erythrocytes

Batch 2: Poly (I: C) and ovalbumin-loaded erythrocytes

Batch 3: unloaded erythrocytes

The batches are injected intravenously to C57Bl/6 mice (10 mice per group). Seven days after batch injection, $2.2\times10^6$ EG.7 cells per mice are injected subcutaneously. Mice are followed for tumor growth. Tumor growth is assessed by measuring the diameter of the tumor in centimeters (recorded as the average of two perpendicular diameter measurements). Tumor size is measured 3 times per week at 2 days interval during 14 days. Mice with tumors of more than 2.0 cm of diameter are killed.

TABLE 16

| OVA amount injected per mice | |
|---|---|
| Batches | OVA quantity injected to mice (μg) |
| 1 | 134 |
| 2 | 134 |
| 3 | 0 |

TABLE 17

| Tumor growth | | | | | | | |
|---|---|---|---|---|---|---|---|
| | Tumor growth ($mm^3$) the days following tumor cell injection | | | | | | |
| Batches | 0 | 3 | 5 | 7 | 10 | 12 | 14 |
| 1 | 0 | 0 | 0 | 0 | 0 | 0 | 0 |
| 2 | 0 | 0 | 0 | 0 | 0 | 0 | 0 |
| 3 | 0 | 0 | 0 | 363 ± 200 | 756 ± 462 | 1009 ± 445 | 1198 ± 541 |

7 days after EG.7 injection, the size of the tumors is measurable on the flank of the mice previously injected with unloaded erythrocytes and the tumors continue to growth until the end of the study. Whereas no tumors are observed on the flank of the mice injected with Poly (I:C) and ovalbumin-loaded red blood cells treated or not with the anti-TER 119 antibody. Observation of the mice is still ongoing.

In conclusion, these results demonstrate that ovalbumin-loaded red blood cells treated or not with the anti-TER 119 antibody are efficient to prevent the growth of OVA expressing tumor cells.

Example 14. Measurement of the Phagocytosis of Pig Red Blood Cells by Macrophages and Dendritic Cells In Vivo This study is a xenogenic study, since pig red blood cells are injected into C57Bl/6 mice.

The pig red blood cells are washed three times in NaCl containing glucose, before being labelled with CFSE as described above. The red blood cells are washed again three times in NaCl containing glucose, and then brought back to a haematocrit of 50%. A batch of $142\times10^7$ pig red blood cells is injected intravenously into three C57Bl/6 mice. One hour after the injection, the mice are sacrificed and the spleens, the livers and the femurs of the mice are removed. The fluorescence incorporated into the macrophages expressing the F4/80 marker or the CD11b marker, into the myeloid dendritic cells expressing the CD11c and CD11b markers and into the plasmacytoid dendritic cells expressing the CD11c and CD8 markers is measured by flow cytometry.

Batch 1: pig red blood cells

Batch 2: NaCl containing glucose

Results

TABLE 18

| Percentage of spleen macrophages or dendritic cells having phagocytosed fluorescent red blood cells 1 hour after injection: | | | | |
|---|---|---|---|---|
| Batches | F4/80 macrophages | CD11b macrophages | Myeloid dendritic cells | Plasmacytoid dendritic cells |
| 1 | 27 ± 6 | 4 ± 2 | 21 ± 5.5 | 45 ± 6 |
| 2 | 0 | 1 | 4 | 3 |

TABLE 19

| Percentage of bone marrow macrophages or dendritic cells having phagocytosed fluorescent red blood cells 1 hour after injection: | | | | |
|---|---|---|---|---|
| Batches | F4/80 macrophages | CD11b macrophages | Myeloid dendritic cells | Plasmacytoid dendritic cells |
| 1 | 5.3 ± 7.5 | 0.8 ± 1 | 5 ± 3 | 5 ± 7 |
| 2 | 6.3 | 0 | 6 | 12.9 |

TABLE 20

| Percentage of liver macrophages or dendritic cells having phagocytosed fluorescent red blood cells 1 hour after injection: | | | |
|---|---|---|---|
| Batches | CD11b macrophages | Myeloid dendritic cells | Plasmacytoid dendritic cells |
| 1 | 1.1 ± 1.1 | 3 ± 2.8 | 1.2 ± 1 |
| 2 | 1.7 | 3.4 | 0.7 |

One hour after injection, the pig red blood cells were efficiently phagocytosed by the F4/80 macrophages and the dendritic cells of the spleen (Table 18). The plasmacytoid dendritic cells of the spleen are the cells most involved in the phagocytosis of the pig red blood cells. In the bone marrow and the liver, the macrophages and the dendritic cells did not phagocytize fluorescent red blood cells (Tables 19 and 20).

In conclusion, the use of pig red blood cells allows targeting and phagocytosis of the red blood cells by the spleen cells involved in the generation of immune responses (Lou Y., 2007, J of Immunol, 178: 1534-1541).

Example 15. Characteristics of Pig Red Blood Cells Comprising Ovalbumin

Two batches were prepared of pig red blood cells which had either been charged with ovalbumin (obtained in accordance with variant 2 of Example 1) or had not been charged therewith.

Batch 1: Pig red blood cells charged with OVA

Batch 2: Pig red blood cells not charged with OVA.

Batches from the starting material were characterized at the end of production and 18 hours after production. The mean globular volume, the mean corpuscular haemoglobin and the concentration of red blood cells was measured using an ABX cell counter. The osmotic fragility, which corresponds to the concentration of NaCl inducing 50% haemolysis of red blood cells, was measured using an Osmocells instrument (SD Medical). The extracellular haemoglobin was measured by spectrophotometry. The corpuscular concentration of ovalbumin, the extracellular concentration of ovalbumin and the mean globular quantity of ovalbumin were determined using an ELISA test.

TABLE 21

Characteristics of pig red blood cells comprising ovalbumin:

| | Day of production | | | 18 hours after production | | |
|---|---|---|---|---|---|---|
| Characteristics | Starting material | Batch 1 | Batch 2 | Starting material | Batch 1 | Batch 2 |
| Mean globular volume ($\mu m^3$) | 65 | 55 | 57 | 65 | 56.0 | 58 |
| Mean corpuscular haemoglobin (g/dl) | 31.9 | 27.7 | 25.9 | 31.4 | 28.9 | 25.8 |
| Osmotic fragility (salinity inducing 50% haemolysis in g/l of NaCl) | | | | 3.98 | 2.51 | 3.33 |
| Haematocrit of suspension (%) | 36.8 | 48.2 | 50 | 36.5 | 46.3 | 48 |
| Concentration of red blood cells ($10^6/mm^3$) | 5.64 | 9.1 | 8.1 | 5.9 | 9 | 8.4 |
| Extracellular haemoglobulin (g/dl) | 0.04 | 0.27 | 0.196 | 0.05 | 0.79 | 0.56 |
| Corpuscular ovalbumin concentration (mg/ml of red blood cells) | | 0.66 | 0 | | 0.71 | 0 |
| Extracellular ovalbumin concentration (mg/ml of end product) | | 0.02 | 0 | | 0.02 | 0 |
| Mean globular quantity ($mg/10^9$ GR) | | 0.03 | 0 | | 0.04 | 0 |

As expected, the dialysis procedure caused a reduction in the globular volume and the corpuscular haemoglobin. Furthermore, the osmotic fragility of the batches was lower than that of the red blood cells of the initial blood (Table 21). No major differences were observed between the batch comprising the ovalbumin (batch 1) and that which did not comprise it (batch 2).

For batch 1, the quantity of extracellular ovalbumin was relatively low compared with the quantity of encapsulated ovalbumin and had not increased 18 hours after production, thereby demonstrating the stability of the red blood cells encapsulating the ovalbumin.

Thus, it is possible to encapsulate ovalbumin in pig red blood cells.

What is claimed is:

1. A method of treating cancer comprising administering to a patient in need thereof an effective amount of a non-naturally-occurring suspension of red blood cells encapsulating a tumor antigen inside of said red blood cells, and an adjuvant for activating dendritic cell maturation.

2. The method of claim 1, comprising inducing in a patient a cytotoxic cellular response against tumor cells or a tumor as a result of administering to said patient an effective amount of the non-naturally-occurring suspension of red blood cells encapsulating a tumor antigen inside of said red blood cells, and the adjuvant for activating dendritic cell maturation.

3. The method according to claim 1, wherein the red blood cells (1) encapsulate said tumor antigen and (2) are in the form of an immune complex with an immunoglobulin which recognizes an epitope at the surface of the red blood cells, so as to promote phagocytosis of said red blood cells by dendritic cells.

4. The method according to claim 3, wherein the red blood cells form an immune complex with an anti-rhesus or anti-glycophorin A or anti-CR1 antibody.

5. The method according to claim 1, wherein the red blood cells (1) encapsulate said tumor antigen and (2) are heat-treated or chemically treated so as to promote phagocytosis of said red blood cells by dendritic cells.

6. The method according to claim 1, wherein the adjuvant is present in the red blood cells, at their surface and/or outside the red blood cells.

7. The method according to claim 6, wherein the adjuvant is a TLR (Toll-like receptor) ligand or a cytokine.

8. The method according to claim 7, wherein the TLR ligand is an imidazoquinoline selected from the group consisting of imidazoquinoline, imiquimod, resiquimod, CpG oligodeoxynucleotides LPSs (lipopolysaccharides) and poly(inosinic acid)-poly(cytidylic acid).

9. The method according to claim 7, wherein the cytokine is selected from the group consisting of interferon alpha, IL-2 (interleukin 2), IFNγ (interferon gamma), GM-CSF (Granulocyte Monocyte-Colony Stimulating Factor), IL-12 (interleukin 12) and TNFα (Tumor Necrosis Factor alpha).

10. The method according to claim 1, comprising at least two tumour antigens representative of the tumour to be treated.

11. The method according to claim 1, wherein the tumour antigen is an antigen selected from the group consisting of alpha-actinin-4; ARTC1; BCR-ABL fusion protein (b3a2); B-RAF; CASP-5; CASP-8; beta-catenin; Cdc27; CDK4; CDKN2A; COA-1; dek-can fusion protein; EFTUD2; Elongation factor 2; ETV6-AML1 fusion protein; FN1; GPNMB; LDLR-fucosyltransferaseAS fusion protein; HLA-A2d; HLA-A11d; hsp70-2; KIAAO205; MART2; ME1; MUM-1f; MUM-2; MUM-3; neo-PAP; Myosin class I; NFYC; OGT; OS-9; pml-RARalpha fusion protein; PRDX5; PTPRK; K-ras; N-ras; RBAF600; SIRT2; SNRPD1; SYT-SSX1 or -SSX2 fusion protein; Triosephosphate Isomerase; BAGE-1; GAGE-1,2,8; GAGE-3,4,5,6,7; GnTVf; HERV-K-MEL; KK-LC-1; KM-HN-1; LAGE-1; MAGE-A1; MAGE-A2; MAGE-A3; MAGE-A4; MAGE-A6; MAGE-A9; MAGE-A10; MAGE-A12; MAGE-C2; mucin k; NA-88; NY-ESO-1/LAGE-2; SAGE; Sp17; SSX-2; SSX-4; TRAG-3; TRP2-INT2g; CEA; gp100/Pme117; Kallikrein 4; mammagolbulin-A; Melan-A/MART-1; NY-BR-1; OA1; PSA; RAB38/NY-MEL-1; TRP-1/gp75; TRP-2; tyrosinase; adippohilin; AIM-2; BING-4; CPSF; cyclin D1; Ep-CAM; EphA3; FGF5; G250/MN/CAIX; HER-2/neu; IL13Ralpha2; Intestinal carboxyl esterase; alpha-foetoprotein; M-CSF; mdm-2; MMP-2; MUC1; p53; PBF; PRAME; PSMA; RAGE-1; RNF43; RU2AS; secemin 1; SOX10; STEAP1; survivin; Telomerase; WT1; FLT3-ITD; BCLX(L); DKK1; ENAH(hMena); MCSP; RGSS; Gastrin-17; Human Chorionic Gonadotropin; EGFRvIII; HER2; HER2/neu; P501; Guanylyl Cyclase C; and PAP.

12. The method according to claim 1, comprising administering the suspension of red blood cells at a haematocrit level of between 40 and 70%.

13. The method according to claim 1, comprising administering the suspension of red blood cells at a haematocrit level of between 45 and 55%.

14. The method according to claim 1, comprising administering the suspension of red blood cells in a volume of 10 to 250 ml.

15. The method according to claim 1, comprising administering the suspension intravenously by injection or infusion.

16. The method of claim 1, wherein the suspension comprises saline buffer comprising NaCl and an ingredient selected from the group consisting of adenine, glucose and mannitol.

17. The method as claimed in claim 1, wherein the suspension comprises a saline buffer comprising NaCl, adenine, glucose and mannitol.

18. The method as claimed in claim 1, wherein the suspension is packaged into a blood bag suitable for blood transfusion.

19. The method as claimed in claim 1, wherein the blood bag contains the amount of encapsulated tumour antigen corresponding to the medical prescription.

20. The method as claimed in claim 1, wherein the adjuvant is encapsulated inside the red blood cells encapsulating the tumor antigen.

21. The method as claimed in claim 1, wherein the adjuvant is encapsulated inside red blood cells.

22. The method as claimed in claim 1, wherein the suspension comprises a NaCl glucose buffer.

* * * * *